United States Patent
Dawson, Jr. et al.

[11] Patent Number: 5,947,906
[45] Date of Patent: Sep. 7, 1999

[54] APPARATUS FOR ENHANCED VISUAL VENOUS EXAMINATION

[76] Inventors: Fredric O. Dawson, Jr., 1401 Newport Ave., San Jose, Calif. 95125; Joel Esparza, 4930 National Ave. #7, San Jose, Calif. 95124-4921

[21] Appl. No.: 08/970,466

[22] Filed: Nov. 14, 1997

[51] Int. Cl.⁶ .............................. A61B 5/05; G01J 3/50
[52] U.S. Cl. ...................... 600/473; 600/476; 250/226; 356/51
[58] Field of Search ........................ 600/473, 476; 250/330, 332, 226, 341.8, 574; 348/77, 162, 164; 356/51; 606/130

[56] References Cited

U.S. PATENT DOCUMENTS

| | | |
|---|---|---|
| 4,442,844 | 4/1984 | Navach . |
| 4,817,622 | 4/1989 | Pennypacker ........................ 128/664 |
| 4,898,175 | 2/1990 | Noguchi . |
| 4,911,544 | 3/1990 | Walsh . |
| 4,945,409 | 7/1990 | Nakamura . |
| 5,074,306 | 12/1991 | Green et al. . |
| 5,519,208 | 5/1996 | Esparza . |
| 5,608,210 | 3/1997 | Esparza . |

*Primary Examiner*—George Manuel
*Assistant Examiner*—Shawna J. Shaw
*Attorney, Agent, or Firm*—Robert Samuel Smith

[57] ABSTRACT

An apparatus for aiding in performing operations requiring location of blood vessels such as intravenous injections or drawing blood in which a charge coupled device camera is focused on an area of the body such as the arm that is illuminated by a light source which emits light that is partly in the infrared range and partly in the ultraviolet range but from which light light having a wavelength in the visible range has been substantially eliminated. The useful range of wavelengths may be provided by any one of several methods including having an infrared source and an ultra violet source or an incandescent source emitting wavelengths extending from the infrared to the ultra violet and having a filter for removing the range of visible light.

5 Claims, 2 Drawing Sheets

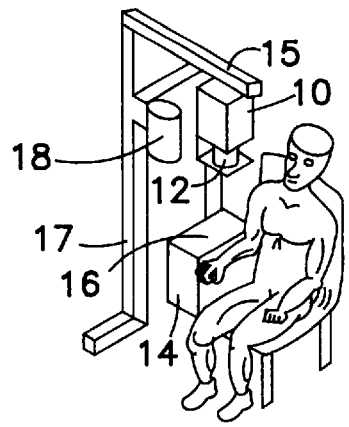 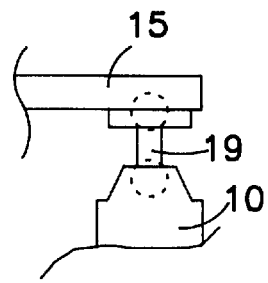
FIG. 1A  FIG. 2B
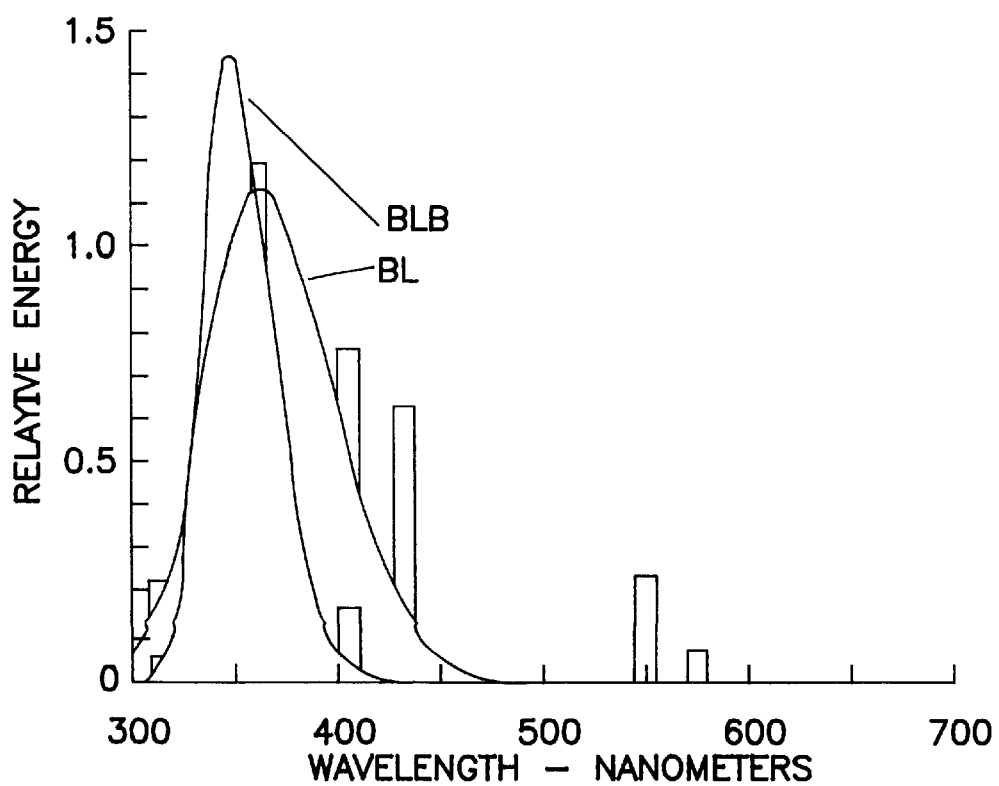
FIG. 2

APPARATUS FOR ENHANCED VISUAL VENOUS EXAMINATION

FIELD OF THE INVENTION

This invention relates to visual examination of the features of the human body such as the venous system and particularly to improvements in the method of gaining intravenous access by enhancing the view of the venous system.

BACKGROUND AND INFORMATION DISCLOSURE

The difficulties of gaining intravenous access such as for drawing blood, intravenous fusion, etc., are well known to vary from one patient to another. Some patients have very prominent veins and this situation simplifies the procedure although, even for some of these patients, their veins have a tough resiliency that makes the veins difficult to penetrate with a hypodermic needle. In the context of this specification, the term, hypodermic needle, will be understood to mean any access device such as a syringe with needle for drawing blood, intravenous catheter, etc. In other patients, the veins are small, deepest, and scarcely visible so that gaining intravenous access is very unpleasant for both the practitioner and the patient. The complexion of the patient can be another troublesome factor. For example, the veins of Afro-Americans are not nearly as visible as the veins of many other patients which hinders the process of finding a vein and drawing blood therefrom. Infants have immature vascular development. Obese patients have venous structure that is difficult to penetrate. At the very least, these complications can greatly increase the stress experienced by the patient. At worst, delays in gaining intravenous access can result in death.

U.S. Pat. No. 4,817,612 to Pennypacker et al discloses an arrangement shown in FIGS. 1 and 2 (prior art) for locating vascular structures V including a conventional video display D having a monitor screen M, viewed by the eye of an observer through a lens system 14. A mirror 16 deflects an image through filter F to camera C which includes a charged coupled device 20 with lens system 22. A problem with the arrangement of FIGS. 1 and 2 is that the device must be supported by placing the bottom edge of the mirror 16 against the surface of the limb of the patient. This is not an acceptable practice for many situations. A second problem is that placement of the mirror 16 in the vicinity of the patient interferes with applying the hypodermic needle to the required location on the patient. A third consideration is a limited range of location for placement of the light L of the Pennypacker system. A fourth consideration is the requirement that the patient remain motionless for an extended period of time in one location which is a difficult requirement for small children. A fifth consideration is that the cost of the Pennypacker device, including the half silvered mirror and optical system for reflecting an image of the area of interest onto the camera is greater than the cost of the present invention.

U.S. Pat. No. 5,519,208 to Esparza et al discloses a lamp means radiating an area of the body and a mirror for reflecting only wavelengths selected to enhance the venous image of the area so that an operator is guided to that area of the skin.

U.S. Pat. No. 5,608,210 to Esparza et al discloses a head set containing a CCD camera (charge coupled device)

All of these devices rely on the discovery that the veins and arteries absorb infrared light more strongly than areas of the skin that do not contain veins. Use of these devices is characterized by the following problems:

1. The darker the skin, especially with Afro-Americans, the less is the contrast of venous areas compared to nonvenous areas when viewed with these devices of the prior art. This makes it difficult to see any but the most prominent veins in many patients.
2. The arrangement of the equipment, i.e., camera, mirrors, lens stands, etc., mitigates the convenience necessary for performing an efficient operation.
3. The presence of these paraphenalia is intimidating to the patient, especially a child, and adds to his discomfort of the whole procedure.

SUMMARY

It is an object of this invention to enhance the convenience and reduce the discomfort for the patient of the process of hypodermic intravenous invasion for such purposes as taking samples of blood and performing intravenous injections.

This invention is directed toward a method and apparatus for presenting on a monitor, an image of an area of skin of a patient in which the venous structure is more prominently displayed than with devices of the prior art. The apparatus includes:

a CCD camera;

a filter mounted on the camera that blocks out light in the predominantly visible wave length range and transmits light having a wavelength in the ultraviolet and infrared wavelength range;

a source of light which emits light in the infrared range, the visible wavelength range and the ultraviolet wavelength range.

The invention resides in the discovery that the combination of both these wavelength ranges enhances the venous structure with much greater contrast than infrared alone as taught by the prior art. Furthermore, irradiating the subject with visible light while filtering out visible light to the CCD improves contrast of the CCD and enables the operator to perform his/her tasks in normal light.

BRIEF DESCRIPTION OF THE FIGURES

FIG. 1A shows an arrangement of the invention.

FIG. 1B shows the universal joint mounting camera to frame.

FIG. 2 shows a spectral curve for incandescent light.

DESCRIPTION OF A BEST MODE

Figure 3:
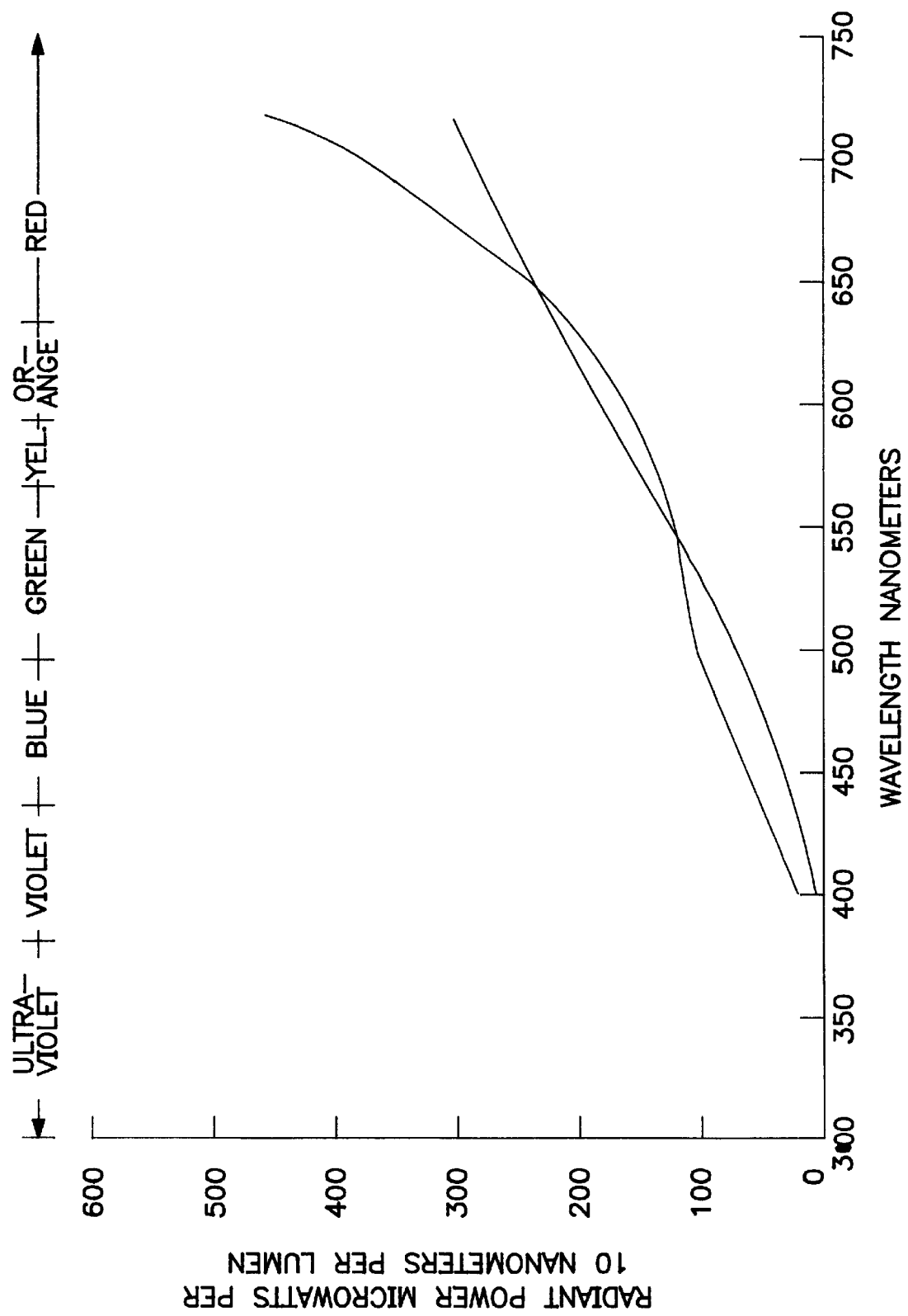
FIG. 3 shows a spectral curve for "black" light.

Turning now to a discussion of the drawings, FIG. 1 shows a CCD video camera 10 positioned to scan the area of the patient to be examined. The camera 10 is attached to an aim 15 of frame 17 by universal joint 19 shown to best advantage in FIG. 1B. The camera lens is equipped with a zoom lens 12 that permits first scanning a large area to identify a preferred region and then enlarging the image of the region to improve the precision in performing the operation. A monitor 14 with the screen 16 for displaying the image is located in a position for convenient viewing of the area of interest by the attendant performing the operation. For many operations where the patient is seated in a chair with his/her arm resting on the aim of the chair, the monitor is placed with the screen next to the patients arm and viewable from an overhead position as as shown in FIG. 1.

Also shown in FIG. 1 is a source 18 of light illuminating the area of interest.

The spectrum of light reflected from the area of interest that forms the image in the camera is a combination of far infrared and ultraviolet light. Preferably, the ultraviolet has a wavelength range shorter than 450 nanometers and the infrared has a wavelength range of greater than 700 nanometers. Radiation having a wavelength between these two ranges is substantially visible light and the presence of wavelengths in this visible wavelength range greatly washes out the image and reduces the contrast between the image of the venous and non venous areas of the skin. The contrast is particularly enhanced with Afro-Americans and other patients having darkly pigmented skin.

The selection of the wavelength ranges according to the invention can be achieved by several arrangements all of which are embodiments of the invention, including:

1. Irradiating the area of interest with an incandescent source which emits a broad spectrum of wavelengths extending from the far infrared to the short ultraviolet and attaching to the camera lens a filter that filters out the visible light range.
2. Irradiating the area of interest with one light source radiating infrared light and simultaneously another source radiating ultraviolet light,
3. Irradiating the area of interest with one light source radiating infrared light and simultaneously another source radiating ultraviolet light and attaching to the camera lens a filter that filters out the visible light range and transmits infra red and ultraviolet.

The third method has been found to be the most effective. The most effective filter that has been used for the purposes of this invention is the Kodak 87C Wratten filter which is very effective in filtering out visible light.

A light source that is suitable for providing the ultraviolet (black light) radiation for purposes of the invention is commonly referred to as GROWLIGHT and is used to grow plants indoors. The spectral distribution of the ultraviolet source used in the invention is shown in FIG. 2. The spectral distribution of an incandescent light is shown in FIG. 3. FIG. 3 shows that the incandescent light emits infrared radiation with wavelength longer than 700 nm and some ultraviolet light (shorter wavelength than 450 nanometers) however the energy distribution in this range is not as strong as the spectral distribution in FIG. 2.

An embodiment of this invention is a camera mount 11 that enables the operator to swivel the camera in a broad range of directions and to rotate the camera 180° about an axis coincident with the centerline of the camera lens. These features are very useful for working with patients that must be kept perfectly immobile. It is also useful in providing the operator options to select a direction of motion of the image right or left, up or down, relative to the direction of movement of his instrument. The camera is supported by a universal joint 19 such as a cup and ball joint on the end of an arm extending from a base column so that the camera may be positioned over the patient.

As disclosed above, the contrast between venous and non venous areas is particularly dramatic for dark skinned people, especially Afro-Americans. Although I do not wish to be bound by theory, this observation suggests the following mechanism as to how the invention performs its function:

The ability of the skin to prevent the absorption of ultraviolet radiation depends on the melanin content of the skin. Melanin is a natural dark pigment (polymer) that is found in all skin but in greater concentration in dark skin. Exposure to sunlight induces an increase in melanin which is recognized as "tan". The photoprotective role of melanin is believed to be related to the ability of this polymer to attenuate the impinging ultraviolet radiation by scattering and degrading it to heat. The fact that the contrast between venous and nonvenous area is more pronounced with black skin indicates that the the phenomenon cannot be explained by simple enhanced absorption of infrared radiation by the venous area compared to the nonvenous area otherwise, contrast would be less (rather than more) with dark skin. A possible explanation is that the melanin absorbs the ultraviolet component and that the accompanying infrared induces or hastens the return of the absorbing mechanism to the ground state so that an increased amount of infra red radiation is emitted in the nonvenous areas The above paragraphs disclose embodiments which achieve objects of the invention. One of the important advantages of the invention over the prior art is that the invention can be used in normal or nearly normal illumination in contrast to devices of the prior art utilizing solely infrared and which work best in a darkened environment. Modifications and variations of the invention may be suggested by studying the drawings and reading the specification which are within the scope of the invention. I therefore wish to define the scope of my invention by the appended claims.

We claim:

1. An apparatus for presenting to a user a video view of a venous structure underlying skin in an area of a patient's body while simultaneously permitting direct visual and manual access to said skin which comprises:

an incandescent lamp emitting light in a wavelength range extending from far infrared to ultraviolet black light and arranged to illuminate said area of said patient's body;

a video monitor;

a charge coupled camera connected to said video monitor and having a lens arranged for viewing said venous structure underlying skin by light reflected from said skin;

a filter interposed between said skin and said lens of said camera wherein said filter prevents transmission to said lens of light having a wavelength in a visible range and permits transmission in said far infrared range and said ultraviolet range;

means for supporting said camera, light source and video monitor in a position to form an image on a screen of said video monitor by said charge coupled camera using said light reflected from said area of skin whereby there is presented to the user a view on the video monitor of a venous structure underlying skin in an area of a patient's body while simultaneously permitting direct visual and manual access to the area.

2. The apparatus of claim 1 wherein said lens is a zoom lens.

3. An apparatus for aiding in operations requiring the mapping of venous structure of an area of skin of a patient which comprises:

an incandescent lamp emitting light in a wavelength range extending from far infrared to ultraviolet black light;

a video monitor;

a charge coupled camera connected to said monitor and having a lens for viewing said area;

a filter interposed between said area and said lens of said camera wherein said filter prevent transmission of light having a wavelength in a visible range but permits transmission in said far infrared range and said ultraviolet range.

4. The apparatus of claim 1 wherein said ultraviolet black light has a range of wavelengths shorter than 450 nanometers and said far infrared light has a range of wavelengths greater than 700 nanometers.

5. The apparatus of claim 1 wherein said means for support comprises:
- a stand having one end supportable on a horizontal surface;
- an arm having one end secured to another end of said stand;
- A universal joint means coupling said camera to another end of said arm providing that said camera may be positioned in any orientation convenient for permitting visual and manual access to said area of skin.

* * * * *